United States Patent [19]
Augurt

[11] 3,991,881
[45] Nov. 16, 1976

[54] STERILE PACK

[75] Inventor: Thomas A. Augurt, Stamford, Conn.

[73] Assignee: Propper Manufacturing Co., Inc., Long Island City, N.Y.

[22] Filed: Jan. 21, 1975

[21] Appl. No.: 542,878

[52] U.S. Cl. .................................. 206/439; 53/38; 93/35 R
[51] Int. Cl.[2] .................. B65D 85/70; B65B 55/10; A61B 19/02
[58] Field of Search ................... 206/363, 210, 439; 229/62

[56] References Cited
UNITED STATES PATENTS

| | | | |
|---|---|---|---|
| 2,075,178 | 3/1937 | Copeman | 206/439 |
| 3,061,087 | 10/1962 | Scrivens et al. | 206/439 |
| 3,093,242 | 6/1963 | Huyck et al. | 206/210 |
| 3,460,742 | 8/1969 | Langdon | 229/62 |
| 3,604,616 | 4/1971 | Greif | 206/363 X |
| 3,669,254 | 6/1972 | Chrysanthis et al. | 229/62 X |

Primary Examiner—Leonard Summer
Attorney, Agent, or Firm—Blum, Moscovitz, Friedman & Kaplan

[57] ABSTRACT

A sterile pack blank is provided which comprises an enclosure determined by a substrate of predetermined porosity and a discrete plastic film overlying the porous substrate. The film and porous substrate are adhesively connected by a cohesive or self-sealing adhesive. The porous substrate is printed with a continuous adhesive track, while substantially an entire surface of the plastic film is adhesive coated. An end flap of the film is folded back upon itself along a fold line to provide access to the enclosure interior. After introduction of an instrument into the enclosure, the film end flap is hingedly connected to the substrate, along respective adhesively coated areas thereof, according to the sealing method of the invention. The adhesive is characterized by the fact that it is self-adhering. Therefore, only interfaced areas of the film and substrate that are respectively coated with the adhesive may be adhesively connected. The adhesive coating on the film is further characterized by a predetermined tack value for thereby providing for secure sterile delivery of an instrument from the pack. The porous substrate is provided, respectively, with exterior and interior sterilization indicators. The indicators comprise respective pairs of steam and ethylene oxide sensitive inks. The exteriorly located indicators are immediately sensitive to the sterile ambience of the pack, while the interiorly located indicators are sensitive to a sterile environment within the pack enclosure.

7 Claims, 10 Drawing Figures

STERILE PACK

BACKGROUND OF THE INVENTION

The instant invention relates to a novel sterile packet for sterilizing medical instruments and the like, and to the method for sealing the instrument in the packet. More particularly, this invention relates to a composite packet having a transparent face and an opaque face provided with interior and exterior sterilization indicators, including means for preventing slippage during sterile delivery of the instrument.

While various sterile packs are commercially available, none includes the requisite combination of desirable qualities. The optimal sterile packet should have interior and exterior sterilization indicators; it should have a positive seal on all sides to avoid contamination; it should include means for preventing slippage of the instrument from the packet interior during sterile delivery thereof; and the substrate of which the pack is fabricated should be suitably porous so as to permit the sterilization medium to sterilize the enclosed instrument, but preclude entry of microorganisms therein. It is also deemed highly desirable to provide a sterile pack that may be opened and closed without contacting the interior side walls thereof.

Accordingly, a sterile pack within the scope of the instant invention includes this combination of advantages, including a novel sealing method. The pack performs highly satisfactorily under conventional steam or ethylene oxide sterilization procedures.

SUMMARY OF THE INVENTION

Generally speaking, in accordance with the invention, a sterile pack blank is provided which comprises an enclosure determined by a substrate of predetermined porosity and a discrete plastic film overlying the porous substrate. The film and porous substrate are adhesively connected by a cohesive or self-sealing adhesive. The porous substrate is printed with a continuous adhesive track, while substantially an entire surface of the plastic film is adhesive coated. An end flap of the film is folded back upon itself along a fold line to provide access to the enclosure interior. After introduction of an instrument into the enclosure, the film end flap is hingedly connected to the substrate, along respective adhesively coated areas thereof, according to the sealing method of the invention.

The adhesive is characterized by the fact that it is self-adhering. Therefore, only interfaced areas of the film and substrate that are respectively coated with the adhesive may be adhesively connected. The adhesive coating on the film is further characterized by a predetermined tack value for thereby providing for sterile delivery of an instrument from the pack.

The porous substrate is provided, respectively with exterior and interior sterilization indicators. The indicators comprise respective pairs of steam and ethylene oxide sensitive inks. The exteriorly located indicators are immediately sensitive to the sterilizing ambience of the pack, while the interiorly located indicators are sensitive to a sterilizing environment within the pack enclosure.

Accordingly, it is an object of this invention to provide a sterile pack having a novel construction.

Another object of the invention is to provide a sterile pack having internal and external indicators for respectively showing a sterile environment within the pack enclosure and a sterile ambience for the pack.

Still another object of the invention is to provide a sterile pack which includes means for preventing slippage of an instrument therefrom to thereby enable sterile delivery of the instrument from the pack.

Yet another object of the instant invention is to provide a novel method for sealing the sterile pack after the instrument is introduced therein.

Still other objects and advantages of the invention will in part be obvious and will in part be apparent from the specification.

The invention accordingly comprises an article of manufacture possessing the features, properties, and the relation of elements which will be exemplified in the article hereinafter described. and the several steps for sealing the article and the relation of one or more of such steps with respect to each of the others thereof, which will be exemplified in the method hereinafter disclosed, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENT

Figure 1:
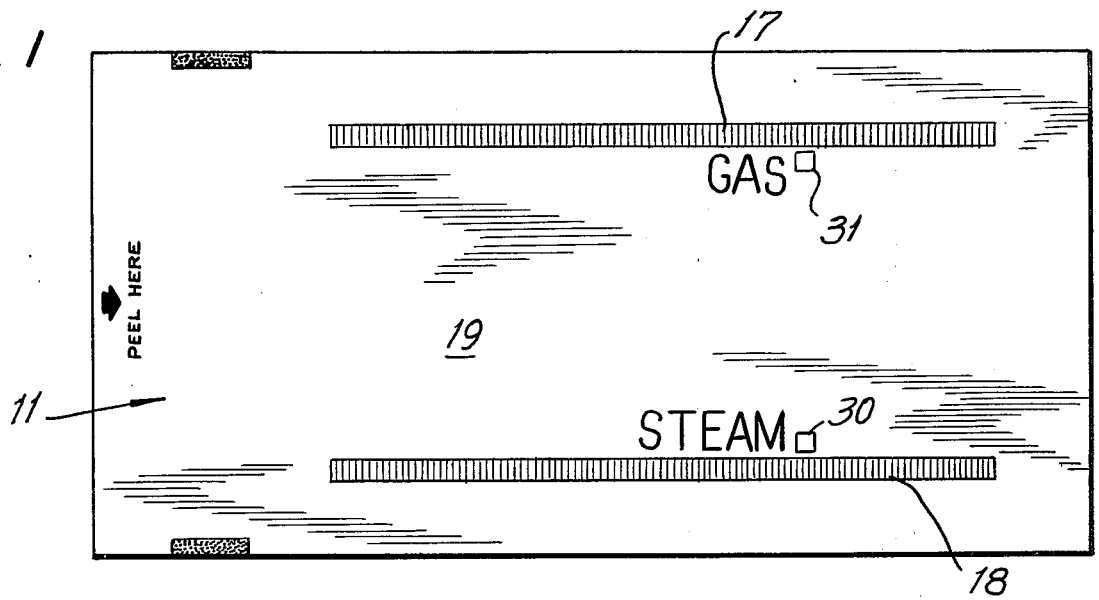
FIG. 1 is a bottom plan view of a sterile pack within the scope of the instant invention.

Referring now to FIGS. 1–3 and 7–10, a non-woven substrate 11, for instance of paper, paper board, fiber-bonded synthetics and the like of generally rectangular shape, is provided with a continuous printed adhesive track 12 along the surface 13 thereof. Adhesive track 12 consisting of an adhesive 12' is of substantially uniform width and, in general, runs along the margin of surface 13 of the substrate. At the top 14 of the packet, substantially symmetrical segments 15, 15' of the track detour acutely inwardly relative to top end 14 of the packet and converge at a vertex 16 for a purpose which will be hereinafter described. Provided in substrate 11 are respective pairs 17, 17' and 18, 18' of sterilization indicators. One member 17, 18 of each respective pair of indicators is located on the surface 19 of substrate 11, and each corresponding member 17', 18' of the pair is located on the surface 13 of substrate 11. As seen in the Figures, respective members of each pair of indicators overlie each other.

Overlying surface 13 of substrate 11 is a discrete substantially rectangular section of a clear plastic film 20, fabricated for instance of high or low density polyethylene, polypropylene or polyethylene-terephthalate. The surface 21 thereof which interfaces with surface 13 of substrate 11 is substantially completely coated with adhesive 12'. Overlapping adhesively coated areas of substrate 11 and film 20 are adhesively connected thereby determining an enclosure 22 into which access may be had through an inlet slot 23.

At top end 14 of the pack, end wall 24 of film 20 is substantially uniformly foreshortened relative to end wall 25 of substrate 11 for a purpose which is hereinafter described. An end flap 26 of film 20 is folded back upon itself along a fold line 27 for thereby defining access slot 23. After introduction of an instrument 28 into enclosure 22, flap 26 may be hingedly connected to substrate 11, along respective adhesively coated areas thereof, according to the sealing method within the scope of the invention.

Figure 2:
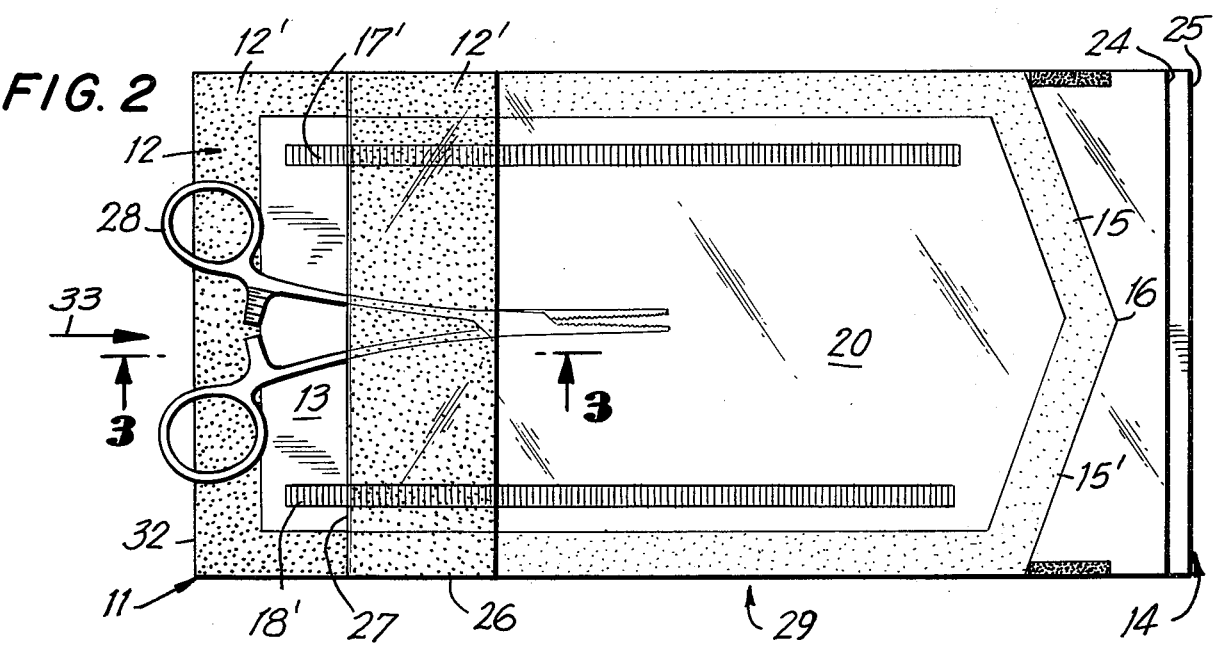
FIG. 2 is a top plan view of the embodiment shown in FIG. 1.

Adhesive 12' is a cold or cohesive seal type commercially available self-adhering adhesive. These adhesives are typically of the rubber latex type. Therefore, only commonly adhesively coated areas of substrate 11 and film 20 may be adhesively sealed. In fabricating the blank 29, as best seen in FIG. 2, adhesive track 12 of substate 11 may be sealed against the adhesively coated surface 21 of film 20 by conventional mechanical means. The interior of surface 13 of substrate 11 is uncoated and therefore presents a foreign substance along its interface with adhesively coated surface 21 of film 20 which does not seal therewith, thereby defining enclosure 22. End flap 26 is overcoated with adhesive 12' and therefore remains free because of the cohesive character thereof, until it is pivoted outwardly into sealed overlying relationship on track 12 of substrate 11. While the cohesive character of adhesive 12' assures that no substantial adhesion occurs between adhesively coated surface 21 of film 20 and instrument 28 introduced into enclosure 22 of blank 29, the adhesive 12' on surface 21 of film 20 is preferably characterized by a predetermined tack for inhibiting accidental slippage of instrument 28 from the pack upon sterile presentation thereof, for thereby assuring sterile delivery of instrument 28.

The statistical likelihood of successful sterile delivery after sterile presentation of instrument 28 is optimized when the tack value of adhesive 12' on surface 21 of film 20 is between about 0.5 to about 60.0 sec., and preferably between about 2.5 and about 12.0 sec., as measured according to a modified version of PSTC-14 (11/70). The modification was introduced to account for the fact that instrument 28 is often stainless steel, tungsten steel and the like. According to the test method 2 × 5 × 1/16 inch stainless steel substrates, type 302, finish No. 4 were provided. The test substrates were scrubbed with surgical gauze saturated with diacetone alcohol, wiped dry, scrubbed a second time with surgical gauze saturated with isopropyl alcohol, and air dried. 2 × 2 inch paper masks were cut (max. paper thickness 0.002 inch) and rectangular windows of 1 × 1 ± 0.01 inches were respectively, provided in the middle thereof.

As test specimens, strips approximately 5 × 1.5 − 1.8 inches, of adhesive coated plastic film, were cut. The test specimens were laid on a flat surface, adhesive side up, and a mask was placed over each specimen whereby the 1 × 1 windows therein covered respective test specimens. The masks were pressed onto respective specimens with care taken to press only the paper surfaces of the masks.

The specimens were lifted by their ends, inverted and placed on respective test substrates, whereby the respective windows thereof were located at the approximate centers of the respective substrates. Each test specimen was pressed onto its substrate by a mechanically operated roller having a rubber covered wheel. The roller weighed 4.5 ± 0.1 lbs., had a diameter of 3.25 ± 0.1 inches, and a width of 2.5 ± 0.1 inches. The rubber surface was approximately ¼ inches thick and had a durometer hardness value of 70–80. The roller was moved over the test specimens at a speed of 12 inches per minute, once forward and once reversed.

A test weight consisting of a narrow metal strip having a 1 × ½ inch adhesive tape attached to an end thereof was provided. A ½ × ½ inch portion of the adhesive tape projected beyond the edge of the metal strip. The test weight, including the adhesive weighed 1 ± 0.01 grams.

Each test specimen was trimmed by cutting it across the narrow side exactly at the edge of the paper mask therein and the excised portion was discarded. The test weight was attached to the edge of the mask at the center of the trimmed side of the test specimen.

While holding the test weight and pressing the mask against the surface of the test substrate, the entire assembly was inverted and horizontally mounted. The pressure securing the test weight against the substrate was gently relieved to avoid imparting a shock load on the specimen, and simultaneously therewith a timer was actuated. The timer recorded until the entire area of the specimen within the 1 × 1 window of the mask was disconnected from the substrate. Values were calculated as set forth in the PSTC-14 test method. Actual values recorded for the test specimens were, respectively, 2.5, 2.5, 3.0, 3.5, 4.0, 12.0, 12.0, 15.5, 52 and 54 seconds. The adhesive composition was a constant for all the tests performed.

It is a significant feature of the invention that the adhesive seal between substrate 11 and film 20 does not breach during the sterilization procedure. In general this feature relates to the variable functional relationship determined to be present between the porosity of substrate 11 and the adhesive value of adhesive 12'. Under typical sterilization conditions, a substrate porosity of between about 10 and about 150 gurlies and preferably from about 18 to 100 gurlies provides highly satisfactory results. The priority, expressed in gurlies, is determined on the Gurley-Hill S-P-S tester and is in seconds/ 100 ml. Higher porosities may render the sterile enclosure accessible to microorganisms, and at lower porosities the integrity of the cohesive seal may be fractured. Concomitantly therewith, a cold seal adhesive having a peel strength of about 10.0 to about 18 oz. before sterilization and about 6.0 to about 14 oz. after sterilization as determined by PSTC-1 (last revised 11/70) is found to have a satisfactory adhesive value under typical sterilization conditions. For high-vacuum and/or pulsing type sterilization procedures, as the porosity of the substrate is decreased, the adhesive value or corresponding peel strength of the adhesive must be proportionately increased so as to avoid breaching the adhesive seal in the pack. The peel strength of the adhesive may be increased, for instance, by overcoating it with a primer or by admixing a conventional adjuvant therewith.

Figure 10:
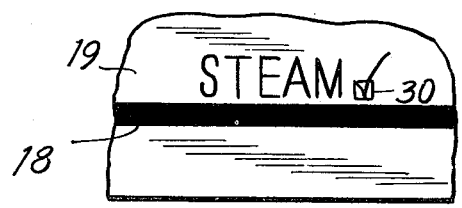

Located above printed indicators 18, 18', as seen in FIGS. 1 and 10 is the legend STEAM, with a recognition blank 30 printed adjacent thereto. When the sterilization procedure to be employed utilizes steam, blank 30 may be marked for thereby directing the technician's attention as to the type of sterilization to be employed. Typically, indicators 18, 18' may be a chemically active ink which changes color after a predetermined period of time upon exposure to pressure steam, such as employed in autoclave sterilization procedures. For instance, the sterilization procedure may trigger a yellow to gray-black color change in indicators 18, 18'. Typical conditions of the color cycle are 4–5 minutes at 272° F. or 20 minutes at about 250° F. Under either set of conditions, sterilization must occur in the substantial absence of air, viz., 98 to 100 percent pure steam.

Figure 9:
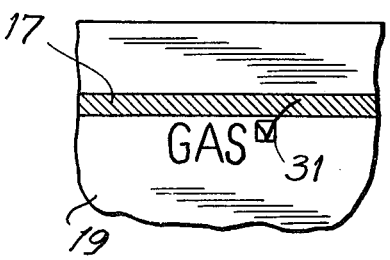
FIGS. 9 and 10 are fragmentary details respectively showing gas and steam indicators provided on the pack.

Alternatively, located below printed indicators 17, 17', as seen in FIGS. 1 and 9, is the legend GAS, with a recognition blank 31 printed adjacent thereto. When the sterilization procedure to be employed utilizes a gas, for instance ethylene oxide, blank 31 may be marked for thereby directing the technician's attention as to the type of sterilization to be employed. Typically, indicators 17, 17' may be a chemically active ink which changes color after exposure to ethylene oxide. For instance, the sterilization procedure may trigger a red to green color change in indicators 17, 17'. A typical color change cycle occurs at 130° F., 50 percent RH, 600 to 700 mgs. of ethylene oxide per liter of sterilizing volume for about 1¾ hours.

The pack is therefore adapted to function within any known sterilizing environment for which its purpose may be suited. It is, moreover, a significant aspect of the invention that indicators 17' and 18' are printed on the substrate surface within the pack enclosure for thereby indicating the presence of a sterilizing environment within the enclosure. This feature safeguards against the incidence of a color change in exterior indicaotrs 17 and 18 before a corresponding color change in indicators 17' and 18' provides notice of a defective production sample, and prevents inadvertent foreshortening of the period of sterilization.

Figure 3:
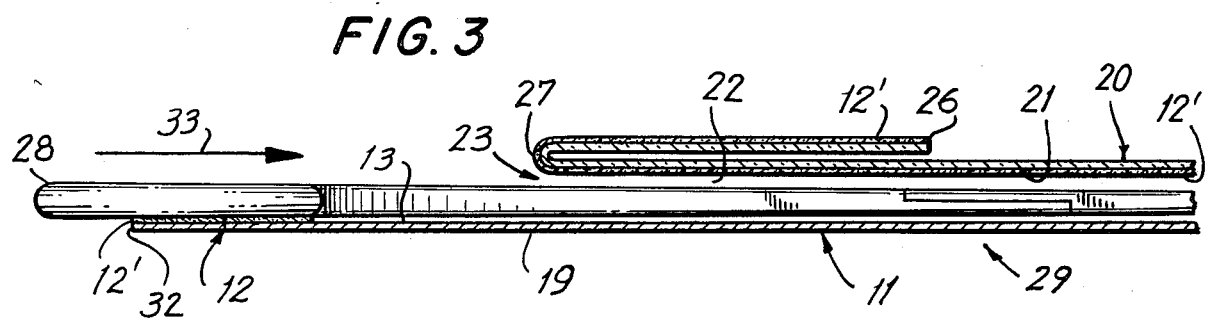
FIG. 3 is a sectional view taken along line 3—3 of the embodiment seen in FIG. 2.
Figure 4:
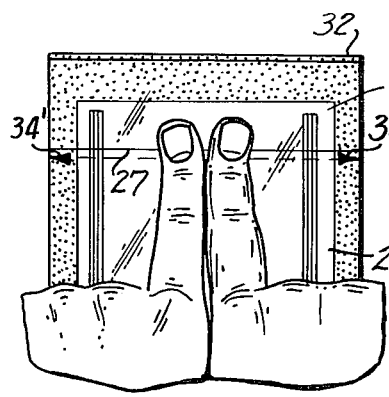
FIGS. 4–6 are detail views sequentially showing method steps for sealing the pack after introduction of the instrument therein.
Figure 5:
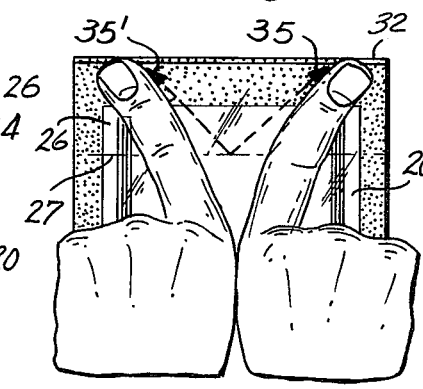
Figure 6:
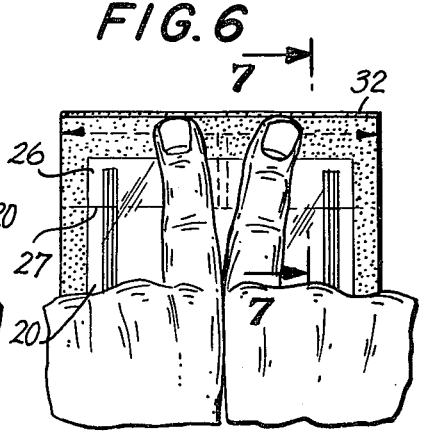

Referring now to FIGS. 2–7, in practice instrument 28 is introduced into blank 29 in the manner best seen in FIGS. 2 and 3. The instrument is introduced into enclosure 22 from the bottom end 32 of the blank in the direction shown by arrow 33. After instrument 28 is introduced into enclosure 22, the pack is sealed from bottom end 32 as best seen in FIGS. 4–6. To seal the pack, it is placed upon a flat surface with film 20 facing upwardly and bottom end 32 facing away from the sealer. The bottom end is manually sealed by placing index fingers under flap 26, thereby rotating it 180° around fold line 27 until it overlies surface 13 of substrate 11. As particularly seen in FIG. 4, the index fingers are centered on fold line 27 and moved toward respective edges of the pack in the respective directions illustrated by arrows 34, 34' for thereby forming the first section of the seal.

As particularly seen in FIG. 5, the second phase of the seal is obtained by replacing the index fingers at the middle of score line 27 facing toward bottom end 32 and each index finger is moved respectively diagonally toward respective opposed corners of bottom end 32 as shown by directional arrows 35, 35'.

To perform the final stage of the sealing operation, the index fingers are returned to their respective positions in the middle of score line 27 and moved initially forwardly to the edge of bottom end 32 and across the edge of bottom end 32 toward the respective opposed corners thereof. Each side seal is secured by running over it with the flat of the index finger then the flat of the finger nail or a smooth hard instrument.

Figure 7:
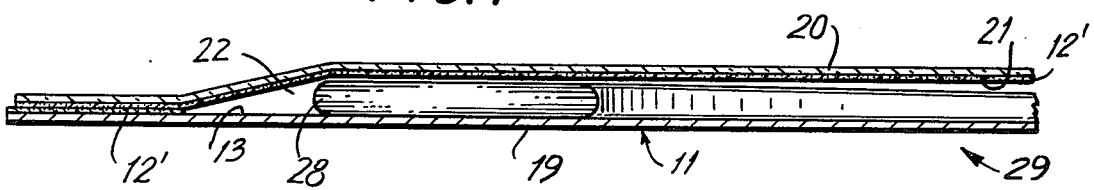
FIG. 7 is a sectional view taken along line 7—7 of FIG. 6 showing an instrument sealed within the pack.
Figure 8:
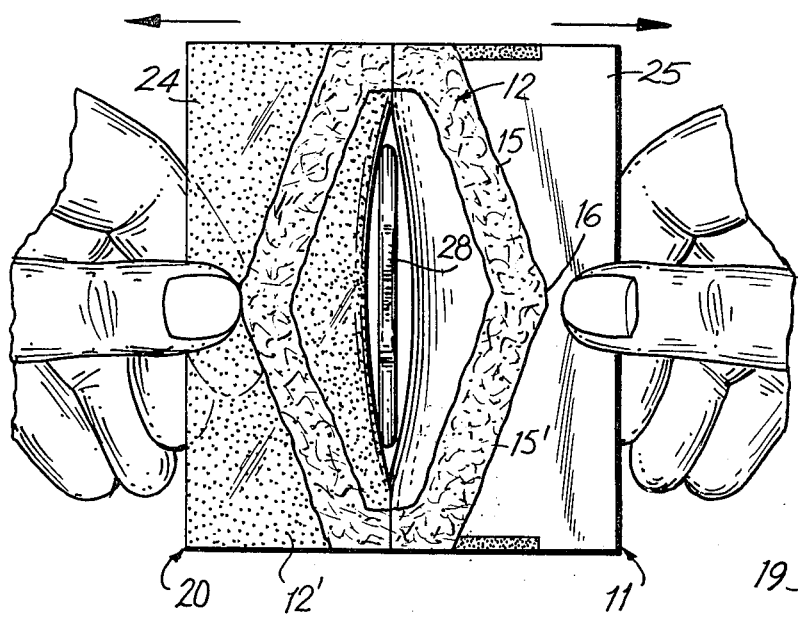
FIG. 8 is a perspective view showing the manner of presentation of the instrument after sterilization.

As best seen in FIG. 7, the pack is in condition for sterile treatment. After the sterile treatment has occurred according to one of the heretofore prescribed procedures, sterile presentation of instrument 28 may be had by respectively gripping end walls 24 and 25 respectively of film 20 and substrate 11 by the thumb and forefinger and applying opposed tensile forces thereon until the opposed tensile forces break the adhesive seal between film 20 and substrate 11 at vertex 16 of track 12. The purpose for configuring track 12 through respective segments 15, 15' is to provide a locus 16 on which opposed tensile forces may act over the smallest area to thereby concentrate the opposed forces for breaking the seal. Upon breaking the seal, additional force is exerted until the adhesive connections along segments 15, 15' of track 12 are breached. Due to their configuration, the opposed tensile forces concentrate upwardly along the track and thereby breach the seal with minimum effort. Once the seal is substantially breached there is a sterile presentation of instrument 28 and sterile delivery thereof may be had as desired.

Thus, it is seen that steps of the sealing method provide a secure seal, and once the bottom end of the pack is adhesively sealed it is not reopened. On the other hand, after completion of the sterilization procedure, the pack may be opened with reasonable facility from the top end for sterile presentation and delivery of the instrument. The tacky interior surface of film 20 prevents slippage of the instrument during sterile delivery thereof. The interior and exterior sterilization indicators provide a double safety check for completion of the sterilization procedure. It is also found that the integrity of the pack is maintained under various sterilization procedures, and within the parameters set forth herein, the pack construction may be modified to accommodate variations in different sterilization procedures.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A sterile pack blank comprising a substrate of predetermined porosity, a discrete plastic film overlying said substrate, said substrate and film being adhesively connected for defining an enclosure therebetween, said enclosure including a sealable inlet thereto, said enclosure defined between said adhesively connected substrate and film having interior and exterior side walls, and at least one pair of sterilization indicators located in said substrate, one member of said pair being arranged on said exterior side wall of said enclosure, and said other member of said pair being arranged on said interior side wall of said enclosure, the two members of each pair of sterilization indicators overlying each other.

2. The sterile pack blank as claimed in claim 1 wherein said substrate is characterized by a porosity of between about 10 and about 150 gurlies.

3. The sterile pack blank as claimed in claim 1 wherein said film includes an adhesively coated surface facing inwardly towards said enclosure, said adhesive coating having a tack value of between about 0.5 and about 60.0 seconds.

4. The sterile pack blank as claimed in claim 1 including an adhesive track of substantially uniform width along a surface of said substrate facing inwardly toward said enclosure, said adhesive track consisting of a cold seal adhesive, said adhesive track including a pair of symmetrical segments which detour acutely inwardly and converge at a vertex substantially at a midpoint of said substrate surface, said track segments being arranged at an end of said substrate which is opposed to an end thereof adapted to adhesively connect with said flap end of said film.

5. The sterile pack blank as claimed in claim 1 wherein said adhesive connection between said substrate and said film is characterized by a before sterilization peel strength of from about 10.0 to 18.0 ounces.

6. The sterile pack blank as claimed in claim 1 wherein said adhesive connection between said substrate and said film is characterized by an after sterilization peel strength of from about 6.0 to about 14.0 ounces.

7. The sterile pack blank as claimed in claim 1 wherein an end of said film opposed to said end thereof in which said end flap is determined is substantially uniformly foreshortened relative to a corresponding end of said underlying substrate.

* * * * *